(12) United States Patent
Hino et al.

(10) Patent No.: US 7,304,179 B2
(45) Date of Patent: Dec. 4, 2007

(54) METHOD FOR PRODUCING METHACRYLIC ACID

(75) Inventors: Tomomichi Hino, Kuga-gun (JP); Akira Ogawa, Tokyo (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 10/569,371

(22) PCT Filed: Aug. 27, 2004

(86) PCT No.: PCT/JP2004/012762

§ 371 (c)(1), (2), (4) Date: Feb. 24, 2006

(87) PCT Pub. No.: WO2005/021480

PCT Pub. Date: Mar. 10, 2005

(65) Prior Publication Data

US 2006/0264668 A1    Nov. 23, 2006

(30) Foreign Application Priority Data

Aug. 29, 2003  (JP) .............................. 2003-307770

(51) Int. Cl.
*C07C 51/16* (2006.01)
(52) U.S. Cl. ...................... 562/532; 562/533; 562/534; 562/535

(58) Field of Classification Search ................. 562/532, 562/534, 535
See application file for complete search history.

(56) References Cited

U.S. PATENT DOCUMENTS

| 4,440,948 | A | * | 4/1984 | Oda et al. | .................... 562/532 |
| 5,719,318 | A | * | 2/1998 | Kawajiri et al. | ............. 562/532 |
| 7,045,657 | B2 | * | 5/2006 | Yunoki et al. | .............. 562/532 |

FOREIGN PATENT DOCUMENTS

| JP | 04-210937 | 8/1992 |
| JP | 2000-070721 | 3/2000 |
| JP | 2003-171339 | 6/2003 |
| JP | 2003-261501 | 9/2003 |
| WO | 01-42184 | 6/2001 |
| WO | 03/055835 | 7/2003 |
| WO | 03/057653 | 7/2003 |

* cited by examiner

*Primary Examiner*—Yvonne Eyler
*Assistant Examiner*—Sudhakar Katakam
(74) *Attorney, Agent, or Firm*—Oblon, Spivak, McClelland, Maier & Neustadt, P.C.

(57) ABSTRACT

The present invention provides a method for producing methacrylic acid through gas-phase catalytic oxidation of methacrolein or a methacrolein-containing gas with molecular oxygen or a gas containing molecular oxygen by the use of a fixed-bed multitubular reactor comprising a plurality of reaction tubes each having a catalyst layer therein, wherein the above catalyst layer is divided in the direction of the tube axis of a reaction tube into two or more layers, to thereby provide a plurality of reaction zones, and the catalyst is caused to be present in the catalyst layer in such a way that a reaction load ratio $CRc(i)$ per unit mass of the catalyst in each reaction zone becomes 0.8 to 1.0.

6 Claims, 2 Drawing Sheets

METHOD FOR PRODUCING METHACRYLIC ACID

TECHNICAL FIELD

The present invention relates to a method for producing methacrylic acid.

The present application claims the priority of Japanese Patent Application No. 2003-307770 filed on Aug. 29, 2003, the contents of which are incorporated herein by reference.

BACKGROUND ART

As it is well-known, there have been many proposals concerning a method for producing methacrylic acid through the gas-phase catalytic oxidation of methacrolein by using a catalyst so far.

Heat accumulation takes place in the catalyst layer because the gas-phase catalytic oxidation is an exothermic reaction. A locally high temperature zone resulting from the heat accumulation is called a hot spot, and when the temperature of this zone becomes higher than it needs, an excessive oxidation reaction takes place so than the yield of the target product is lowered. Consequently, in the industrial enforcement of the aforementioned oxidation reaction, the temperature control of the hot spot is an important subject, and especially when the concentration of methacrolein in the raw gas is raised to increase the productivity, the temperature of the hot spot tends to become high so that a large restriction is forced upon the reaction conditions in the present situation.

Accordingly, there have been several proposals concerning a method for suppressing the temperature of the hot spot so far. For example, a method of packing a plurality of catalysts having different activity in a plurality of reaction zones to order of raise the activity from the inlet part to the outlet part for the raw gas (Patent document 1), a method of packing a catalyst which has a higher compositional ratio of phosphorous and a lower compositional ratio of arsenic nearer to the outlet side for the raw gas (Patent document 2), a method of packing a catalyst which contains a lesser amount of the characteristic element such as potassium nearer to the outlet side for the raw gas (Patent document 3), a method of packing the catalyst wherein a catalyst layer is divided into a plurality of reaction zones, and the activity of the first reaction zone of the inlet side for the reaction gas is adjusted to be higher than that of the second reaction zone, and the activity of the third reaction zone and the zones thereafter are adjusted to be higher in ascending order (Patent document 4), and the like are exemplified.

Patent Document 1: Japanese Patent Application, First Publication No. Hei 4-210937
Patent Document 2: Japanese Patent Application, First Publication No. 2000-70721
Patent Document 3: Japanese Patent Application, First Publication No. 2003-171339
Patent Document 4: Japanese Patent Application, First Publication No. 2003-261501

These are the methods of suppressing the heat value of the reaction per unit volume by lowering the rate of reaction per unit volume at the inlet side for the raw gas in the catalyst layer of the reactor to result in lowering the temperature of the hot spot. Therefore, these are effective in improving the yield by suppressing the consecutive oxidation reaction and in lengthening the catalyst life by reducing the thermal load.

However, these methods only paid attention to suppressing the temperature of the hot spot so that the quantity of oxidation per unit mass of the catalyst in each reaction zone of the catalyst layer has not been controlled at all and consequently the distribution of the load of the oxidation reaction in the catalyst layer has not become uniform and it has been feared that a portion where the load of the oxidation reaction is high may occur. At this portion, the probability of the occurrence of failure in the reoxidation of the catalyst became high, so that deterioration of the catalyst was accelerated and it has been a concern that the life of the catalyst layer as a whole may be drastically shortened.

The present invention has been achieved by taking the above-mentioned problems into consideration and has objects to provide a method for producing methacrylic acid through the gas-phase catalytic oxidation of methacrolein with molecular oxygen in the presence of a solid oxidation catalyst by the use of a fixed-bed tubular reactor, wherein the local deterioration of the catalyst is suppressed and the catalyst is used stably for a long time by not only suppressing the temperature of the hot spot but also making the load of the oxidation reaction in the catalyst layer uniform, and to provide catalyst layers and a fixed-bed multitubular reactor.

DISCLOSURE OF INVENTION

A method for producing methacrylic acid concerning a first embodiment of the present invention is characterized by a method for producing methacrylic acid through the gas-phase catalytic oxidation of methacrolein or a methacrolein-containing gas with molecular oxygen or a gas containing molecular oxygen by the use of a fixed-bed multitubular reactor comprising a plurality of reaction tubes each having a catalyst layer therein, wherein the above catalyst layer is divided in the direction of the tube axis of the reaction tube into two or more layers, to thereby provide a plurality of reaction zones, and the catalyst is packed in such a way that the reaction load ratio per unit mass of the catalyst for each reaction zone falls within a fixed range.

The method for producing methacrylic acid concerning a second embodiment of the present invention is a method in which the packing condition controlling the substantial catalyst-component mass per volume of each reaction zone is determined by the method used in the first embodiment by using the fixed-bed multitubular reactor provided with the reaction tube in which the temperature distribution in the catalyst layer can be measured, and by using the condition thus determined, tee catalyst is packed into the fixed-bed multitubular reactor having the reaction tube in which the temperature distribution in the catalyst layer is not or cannot be measured and methacrylic acid is produced through the gas-phase catalytic oxidation of methacrolein or a methacrolein-containing gas with molecular oxygen or a gas containing molecular oxygen.

In the method for producing methacrylic acid of the present invention, the reaction temperature of the gas-phase catalytic oxidation may be 250 to 350° C.

The aforementioned methacrolein-containing gas may contain 3 to 9% by volume of methacrolein, 5 to 15% by volume of oxygen and 5 to 50% by volume of water vapor and the space velocity of the aforementioned methacrolein-containing gas may be 300 to 3000 $hr^{-1}$.

The maximum value among the distribution of the values obtained by subtracting the aforementioned temperature of the heat transfer medium from the aforementioned temperature in the catalyst layer ($\Delta T$) in the direction of the tube axis of the aforementioned reaction tube may be 35° C. or less.

The aforementioned fixed-bed tubular reactor may be a multitubular reactor provided with a plurality of reaction tubes having an internal diameter of 10 to 40 mm and a heat transfer medium bath.

According to the present invention, in the method for producing methacrylic acid through the gas-phase catalytic oxidation of methacrolein with molecular oxygen in the presence of a solid oxidation catalyst by the use of a fixed-bed tubular reactor, the local deterioration of the catalyst can be suppressed and the catalyst can be used stably for a long time by not only suppressing the temperature of the hot spot but also making the load of the oxidation reaction in the catalyst layer uniform.

BEST MODE FOR CARRYING OUT THE TRENTON

In the present invention, the reaction synthesizing methacrylic acid is performed using a fixed-bed tubular reactor. The aforementioned fixed-bed tubular reactor is provided with a plurality of reaction tubes which are composed of cylinders, a catalyst to be set in each reaction tube to fill at least a part of the cross section of the reaction tube, a catalyst layer formed in the reaction tube including the range where the aforementioned catalyst is positioned, and a gas supplying device which supplies methacrolein or a methacrolein-containing gas and molecular oxygen or a gas containing molecular oxygen to the aforementioned reaction tubes.

Figure 1:
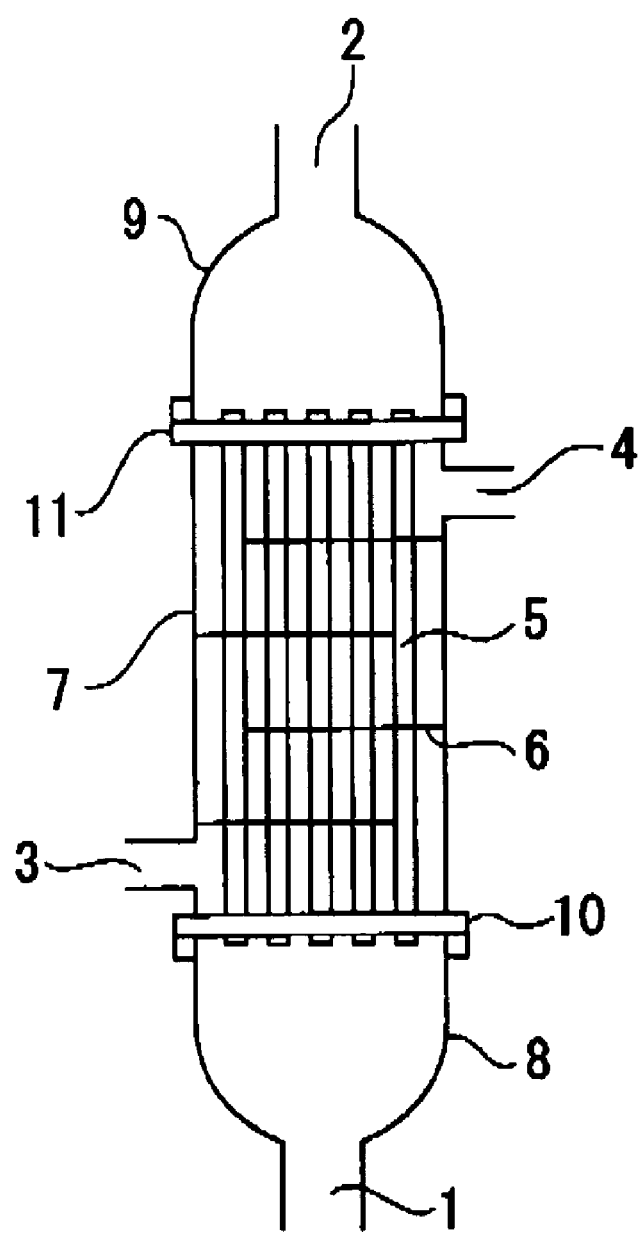
FIG. 1 is a schematic diagram showing a longitudinal section of an example of a fixed-bed multitubular reactor usable in the present invention.

FIG. 1 is a schematic diagram showing a longitudinal section of an example of a fixed-bed multitubular reactor usable in the present invention The fixed-bed multitubular reactor has a cylindrical main body 7, a hemispherical introduction part 8 and a hemispherical derivation part 9 each being fixed at opposite ends of the main body 7 through circular tubesheets 10, 11. A raw gas inlet 1 is formed at the introduction part 8 and a raw gas outlet 2 is formed at the derivation part 9. Between the tubesheets 10, 11, many reaction tubes 5 are fixed parallel to the axis of the main body 7. Owing to this, the raw gas supplied from the raw gas inlet 1 is discharged from the raw gas outlet 2 through the many reaction tubes 5. On the other hand, a heat transfer medium inlet 3 is equipped at one end of the main body 7 while a heat transfer medium outlet 4 is equipped at the other end and the heat transfer medium supplied from the heat transfer medium inlet 3 is discharged from the heat transfer medium outlet 4 passing through the many reaction tubes 5.

Figure 2:
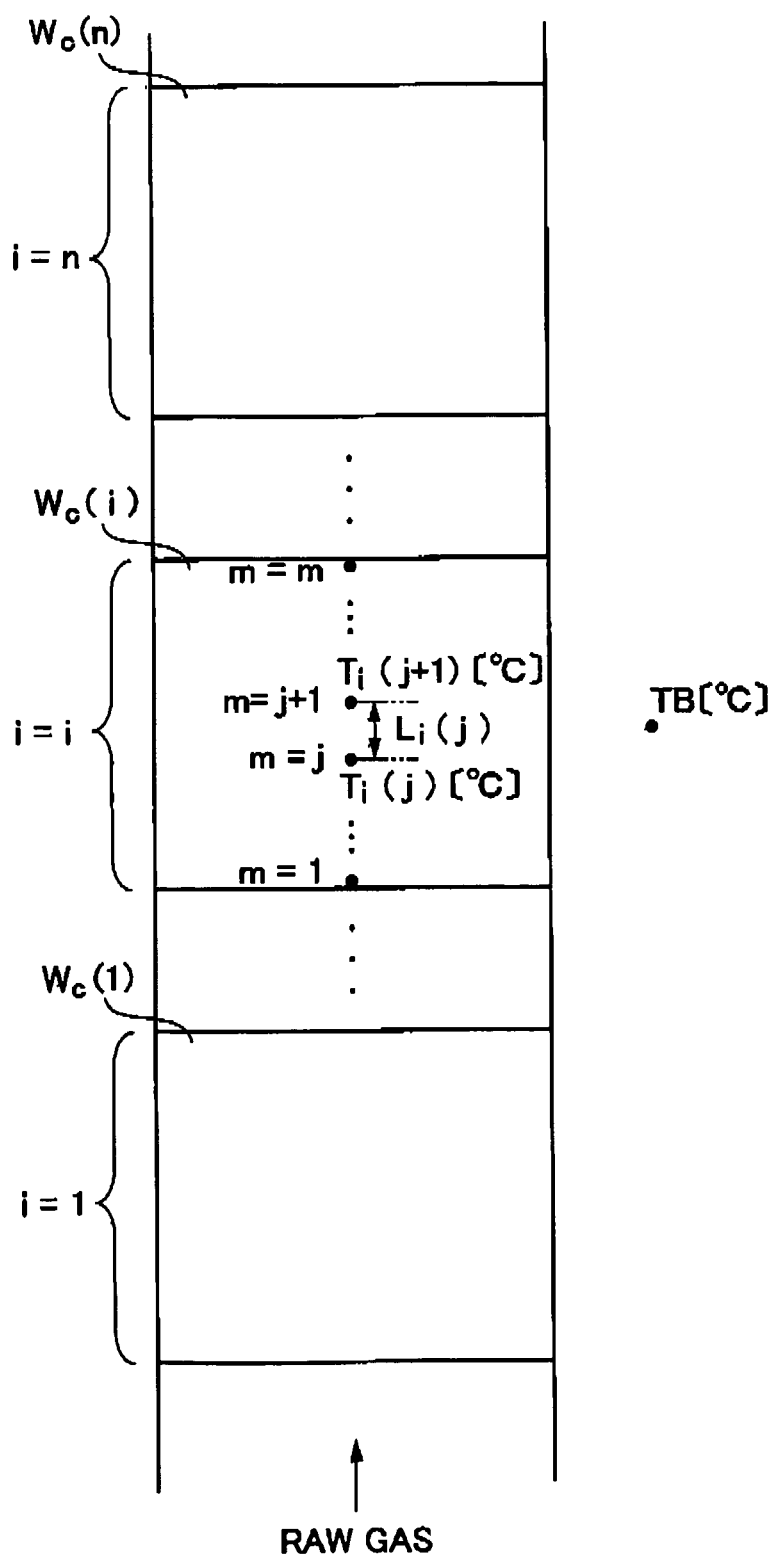
FIG. 2 is a schematic diagram of a longitudinal section of the reaction tube of the aforementioned reactor.

The reaction tube has, as shown in FIG. 2, n layers of reaction zones divided in the direction of the tube axis, the number i (i is an integer from 1 to n) being set to each reaction zone in the sequential order from the upstream side to the downstream side of the raw gas. In each reaction zone, m temperature measuring points are set at intervals in the direction of the axis, the distance between a j th temperature measuring point and a j+1 th temperature measuring point in the sequential order from the upstream side to the downstream side of the raw gas in each reaction zone being represented by Li(j). The temperature of the j th and j+1 th measuring points of the i th reaction zone are represented as Ti(j) and Ti(j+1), respectively. The loading weight of the catalyst of each reaction zone is represented as Wc(i) and the temperature of the heat transfer medium existing among the reaction tubes is represented as TB.

The configurations of these fixed-bed tubular reactors are not particularly limited, but from the industrial point of view, a multitubular reactor provided with thousands to tens of thousands of reaction tubes having an internal diameter of 10 to 40 mm is preferable and a multitubular reactor provided with a heat transfer medium bath is preferable. The heat transfer medium is not particularly limited, and a fused-salt containing potassium nitrate, sodium nitrite and the like is exemplified.

A solid oxidation catalyst is used as the catalyst, and the catalyst is not particularly limited as long as the solid catalyst for oxidation is used and a conventionally known catalyst such as a composite oxide containing molybdenum can be used, however, a composite oxide represented by the following compositional formula is preferable.

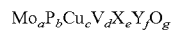

$Mo_aP_bCu_cV_dX_eY_fO_g$ (Wherein Mo, P, Cu, V and O represent molybdenum, phosphorous, copper, vanadium and oxygen, respectively; X represents at least one element selected from the group consisting of iron, cobalt, nickel, zinc, magnesium, calcium, strontium, barium, titanium, chromium, tungsten, manganese, silver, boron, silicon, tin, lead, arsenic, antimony, bismuth, niobium, tantalum, zirconium, indium, sulfur, selenium, tellurium, lanthanum and cerium; Y represents at least one element selected from the group consisting of potassium rubidium, cesium and thallium; subscripts a, b, c, d, e, f and g represent an atomic ratio of each element, respectively; when a is 12, b is in the range of from 0.1 to 3, c is in the range of from 0.01 to 3, d is in the range of from 0.01 to 3, e is in the range of from 0 to 10, f is in the range of from 0.01 to 3 and g represents the atomic ratio of oxygen that fulfills the requirement of the valence of each element above.)

Further, the preparation method of the catalyst to be used is not particularly limited, and conventionally various well-known methods can be used provided that they don't cause undesirable maldistribution of the components. The raw materials to be used in the preparation of the catalyst are not particularly limited either, and nitrates, carbonates, acetates, ammonium salts, oxides, halides and the like of each element can be used in combination. As a raw material for molybdenum, for example, ammonium paramolybdate, molybdenum trioxide, molybdic acid, molybdenum chloride and the like can be used.

The catalyst to be used may be used without a carrier, however, a supported catalyst supported on an inactive carrier such as silica, alumina, silica-alumina, silicon carbide and the like or a catalyst diluted with these inactive carriers can be used.

The catalyst layer refers to a space portion where at least a catalyst is contained in a reaction tube of the fixed-bed tubular reactor. Namely, it refers to not only the space where only the catalyst is packed but also the space where the catalyst is diluted with the inactive carrier and the like. However, a space portion at each end past of the reaction tube where nothing is packed or a space portion where only the inactive carrier is packed is not included in the catalyst layer because the catalyst is not substantially contained.

Now, the reaction for producing methacrylic acid through the gas-phase catalytic oxidation of methacrolein with molecular oxygen in the presence of a solid oxidation catalyst by the use of a fixed-bed tubular reactor is usually carried out under a reaction temperature in the range of from 250 to 350° C. At this time, the reaction raw material is not particularly limited as long as it contains methacrolein and oxygen, however, generally a gas containing 3 to 9% by volume of methacrolein, 5 to 15% by volume of oxygen and 5 to 50% by volume of water vapor (hereinafter merely referred to as a raw gas) is used.

The raw gas to be used here may contain a small amount of impurities which don't exert any substantial influence on the present reaction such as lower saturated aldehydes, ketones and the like, or may be diluted by adding an inert gas such as carbon dioxide and the like. The flow rate of the raw gas is not particularly limited, however, a flow rate wherein the space velocity of the raw gas becomes 300 to 3000 hr$^{-1}$, especially 500 to 2000 hr$^{-1}$, is preferable. The reaction temperature of the aforementioned oxidation reaction is preferably 250 to 350° C., especially 260 to 330° C. The reaction pressure can be taken from a normal pressure to several atmospheric pressures.

In the practical enforcement of the present invention, use of the air as an oxygen source of the raw gas is economically advantageous.

When the raw gas is flowed through the catalyst layer kept at the reaction temperature of 250 to 350° C. in the reaction tube by the use of the aforementioned gas supplying device, an oxidation reaction is carried out in the catalyst layer and methacrylic acid is mainly produced. On this occasion, a substantial amount of the catalyst component per unit volume of the inlet side of the fixed-bed multitubular reactor is reduced to suppress the temperature of the hot spot in the inlet side of the catalyst layer.

As the method for reducing the substantial amount of the catalyst component per unit volume, so far a publicly known technology has been used and, for example, 1) a method in which the catalyst layer is divided into a plurality of reaction zones and the catalyst layer of the gas inlet side is diluted with an inert material, 2) a method it which the catalyst layer is divided into a plurality of reaction zones and a supported rate of the catalyst active material (a mass proportion of the active material per one catalyst) is made larger in ascending order from the gas inlet side to the gas outlet side and 3) a method in which the catalyst layer is divided into a plurality of reaction zones and a size of the catalyst molded article is made smaller in ascending order from the gas inlet side, to the gas outlet side are exemplified.

By carrying out such methods, the temperature of the hot spot inside the catalyst layer is suppressed. As the scope of the definition that the temperature of the hot spot is suppressed, though it differs depending on the reaction system, in accordance with the investigation of the present inventors so far, in the case of producing methacrylic acid through a gas-phase oxidation using a solid catalyst such as these in the present invention, the following is given, wherein the maximum value among the distribution of the values after subtracting the temperature of the heat transfer medium from the temperature in the catalyst layer (ΔT) in the direction of the tube axis of the reaction tube is 35° C. or less. However, because of the foregoing reason, by this method alone it is apprehended that the distribution of the load of the oxidation reaction in the catalyst layer may become inhomogeneous and a high load portion of the oxidation reaction way occur.

Consequently, by using the following method, for example, a substantial mass of the catalyst component per unit volume in the catalyst layer can be optimized: 1) the catalyst layer is divided into a plurality of reaction zones and a substantial mass of the catalyst component per unit volume is controlled in each reaction zone by an optional method such as those mentioned above; 2) the reaction is started using the catalyst layer thus obtained; 3) after the start of the reaction, the temperature of the center of the catalyst layer in each reaction zone is measured and from this result the reaction load ratio CRc(i) in each reaction zone is calculated; and 4) the operations 1) through 3) are repeated so that the CRc(i) becomes in the range of from 0.8 to 1.0, preferably from 0.9 to 1.0 in all reaction zones.

In these operations 1) through 4), the reaction load ratio CRc(i) in each reaction zone is calculated in the following manner using the following equations (1) to (3).

$$CRc(i) = Rc(i)/RcMAX \quad (1)$$

$$Rc(i) = \left[ \sum_{j=1}^{m-1} \frac{\{\Delta T_i(j) + \Delta T_i(j+1)\} \cdot L_i(j)}{2} \right] / Wc(i) \quad (2)$$

$$\Delta T_i(j) = T_i(j) - TB \quad (3)$$

(wherein Rc(i) is the reaction load of the i th layer (° C.·m/kg), Li(j) is the distance (m) from the j th measuring point in the i th catalyst layer to the j+1 th measuring point in the direction of the tube axis, Wc(i) is the packing amount (kg) of the catalyst in the i th layer, Ti(j) is the catalyst-layer temperature (° C.) of the j th measuring point in the i th catalyst layer, TB is the heat transfer medium temperature (° C.), RcMAX is the maximum value of Rc(i), n is the number of the reaction zones, and m is the number of the temperature measuring points in the i th catalyst layer. i is 1 to n. i and j are counted in turn from the inlet side of the reaction gas.)

In the calculation of the CRc(i) by the above-mentioned method, the reaction load is made uniform on the following assumptions: 1) the heat value of the catalyst layer is proportional to the quantity of the oxidation reaction in which the catalyst has taken part; 2) the temperature distribution in the radial direction of the catalyst layer does not exist; 3) the overall heat transfer coefficient between the heat transfer medium and the catalyst layer is constant regardless of the reaction zones; 4) in each reaction zone, the heat brought in by the gas flowing in from the inlet part of the reaction zone or taken out from the outlet part of the reaction zone is not taken into consideration.

By assuming in this manner, the value obtained by subtracting the temperature of the heat transfer medium from the temperature in the catalyst layer (ΔT) and the quantity of the oxidation reaction in which the catalyst has taken part are expressed in a linear relationship, Consequently, by integrating the ΔT from the inlet part to the outlet part of each reaction zone along the direction of the tube axis and dividing the resultant value by the packed catalyst mass in the reaction zone, the load of the oxidation reaction in each reaction zone can be calculated.

On this occasion, depending on a position in the catalyst layer, because there is a slight difference in a proportion of occurrence of the main reaction which produces methacrylic acid and the reaction which produces COx or the other components; and there is more or less a temperature distribution in the radial direction of the catalyst layer, and further, there is a change in the overall heat transfer coefficient by controlling a substantial mass of the catalyst component in each reaction zone, and there is a take out of a small portion of the generated heat in each reaction zone by the reaction gas to the outside of the reaction zone, the above assumptions 1) through 4) do not hold true in the strict sense of the word However, in the method for producing methacrylic acid using the catalyst and the fixed-bed multitubular reactor of the present invention, it is essentially sufficient to optimize the substantial mass of the catalyst component using the result calculated with the above method.

In the case of using the above method in the calculation of Rc(i), the number of divisions of the reaction zone can be optionally selected as long as it is two or more and when increasing the number of divisions, the substantial mass of the catalyst component can be finely controlled. Consequently, the optimization can be performed more easily. However, in case that the number of divisions is increased to more than it needs, it takes a long time to pack the catalyst so that the division of around 2 to 4 is selected industrially.

The temperature in the catalyst layer can be measured by inserting and fixing many thermocouples in the reaction tube and also can be measured by a thermocouple inserted in a protecting tube set up in the center of the cross section perpendicular to the tube axis direction of the reaction tube. On this occasion, it is preferable to have a structure, wherein the inside of the protecting tube is separated from the reaction system and the position of measuring the temperature can be changed by adjusting the length of insertion of the thermocouple.

Further, when measuring the temperate distribution of the catalyst layer of each reaction zone, precision of calculating the reaction load is improved by taking a smaller value of the distance between the temperature measuring points Li(j). However, a larger value of the distance may be taken in the part where the temperature change in the tube axis direction of the catalyst layer is small. When determining the temperature measuring point, both ends of the reaction zone have to be the temperature measuring points and the difference between Ti(j) and Ti(j+1) has to be 5° C. or less.

When occasion demands, there is a case that a substantial mass of the catalyst component per unit mass of a catalyst molded article is different by using properly a supported catalyst or a tabletted catalyst in each reaction zone. In this case, the value of not the mass of the packed catalyst molded article but a calculated substantial muss of the catalyst component in each reaction zone may be taken for Wc(i).

Now, in the present invention, a substantial mass of the catalyst component in each reaction zone is optimized by using the temperature distribution in the catalyst layer obtained by performing the reaction, however, in the case of an industrial fixed-bed multitubular reactor to be used practically, there is a case that the temperature distribution of the catalyst layer cannot be measured in all the reaction tubes. In this case, for example, an optimization of a substantial mass of the catalyst component in each reaction zone is carried out by using a reproduced reaction tube as a mode) of the reaction tube composing the fixed-bed multitubular reactor, and by using the condition thus obtained, the catalyst may be packed in the reaction tube composing the industrial fixed-bed multitubular reactor. Further, as a method of the optimization, without packing the catalyst in the actual reaction tube, the following method may be use wherein the catalyst packing condition is found so that CRc(i) in all the reaction zones comes in the above specified range using a simulator which predicts the temperature distribution in the catalyst layer (a simulation program using a computer). In any case, in the present invention, it is necessary that the reaction load ratio [CRc(i)] per unit mass of the catalyst in each reaction zone in the catalyst layer at the time of the reaction becomes 0.8 g to 1.0, and the process of the optimization of the substantial mass of the catalyst component per unit volume in the catalyst layer is not particularly limited. As mentioned above, by optimizing the substantial mass of the catalyst component tier unit volume in the catalyst layer, the effect of the life extension of the present invention is sufficiently obtained even in the industrial fixed-bed multitubular reactor.

Hereinafter, the method for producing methacrylic acid in the present invention will be entered into details with reference to the following examples.

The term "part" in the examples and in the comparative examples means part by mass. The catalyst component is obtained from the charging amount of the raw materials. As a heat transfer medium of the fixed-bed multitubular reactor, a fused-salt composed of 50% by mass of potassium nitrate and 50% by mass of sodium nitrite was used. The temperature in the catalyst layer is measured by a thermocouple inserted in a protecting tube set up in the center of the cross section perpendicular to the tube axis direction of the reaction tube. At this time, the inside of the protecting tube is separated from the reaction system and the position of measuring the temperature can be changed by adjusting the length of insertion of the thermocouple.

The analysis of the raw gas and the gas produced by the reaction is carried out by gas chromatography. The rate of reaction of methacrolein, the selectivity to the produced methacrylic acid and the yield of methacrylic acid are defined below, respectively.

The rate of reaction of methacrolein (%)=(B/A)×100
The selectivity to methacrylic acid (%)=(C/B)×100
The yield of methacrylic acid (%)=(C/A)×100

Wherein A is a number of moles of supplied methacrolein, B is a number of moles of reacted methacrolein and C is a number of moles of produced methacrylic acid.

EXAMPLE 1

In 300 parts of pure water, 100 parts of ammonium paramolybdate, 2.8 parts of ammonium methavanadate and 9.2 parts of cesium nitrate are dissolved. To the resultant solution, a solution obtained by dissolving 8.2 parts of 85 mass % phosphoric acid in 10 parts of pure water and a solution obtained by dissolving 1.1 parts of telluric acid in 10 parts of pure water are added while stirring and heated to 95° C. while stirring. Then, a solution obtained by dissolving 3.4 parts of copper nitrate, 7.6 parts of ferric nitrate, 1.4 parts of zinc nitrate and 1.8 parts of magnesium nitrate in 80 parts of pure water is added. Further, the mixed solution is sired at 100° C. for 15 minutes and a slurry thus obtained is dried by using a spray dryer.

To 100 parts of thus obtained dried material, 2 parts of graphite is added and mixed and molded by a tableting machine into a pellet shed tablet which has an external diameter of 5 mm and a length of 5 mm. The resultant tablet is calcined under airflow at 380° C. for 5 hours and a catalyst is obtained, The composition of the catalyst in atomic ratio except for oxygen is $Mo_{12} P_{1.5} Cu_{0.3} V_{0.5} Fe_{0.4} Te_{0.1} Mg_{0.15} Zn_{0.1} Cs_1$.

A fixed-bed tubular reactor, equipped with a heat transfer medium bath, having an internal diameter of 25.4 mm made of SUS 304 is used for the reaction. The catalyst layer is divided into two reaction zones. In the gas inlet side reaction zone located at the supplying side of the raw gas, a mixture of 0.62 kg (520 mL) of the catalyst and 240 mL of aluminum spheres having an external diameter of 5 mm is packed. The length of the catalyst layer of the raw gas inlet side reaction zone is 1502 mm.

Then, 0.91 kg (760 mL) of the catalyst is packed in the gas outlet side reaction zone. At this time, the length of the catalyst layer of the gas outlet side reaction zone is 1505 mm.

Then, the heat transfer medium temperature is 312° C. and the raw gas composed of 6.0% by volume of methacrolein, 10% by volume of oxygen, 10% by volume of water vapor and 74.0% by volume of nitrogen is introduced at a space velocity of 170 $hr^{-1}$.

When the temperature of the catalyst layer is measured two days after the start of the reaction, a hot spot having the maximum temperature at the position 400 mm from the upstream end of the gas outlet side reaction zone is observed and $\Delta T$ at the maximum temperature is 32° C. $Rc(i)$ of the raw gas inlet side reaction zone is 52.6° C.·m/kg, $CRc(i)$ is 1.0, $Rc(i)$ of the raw gas outlet side reaction zone is 48.7° C.·m/kg and $CRc(i)$ is 0.93. The rate of reaction of methacrolein is 83.60%, the selectivity to methacrylic acid is 84.4% and the yield of methacrylic acid is 70.6%. Even at 30 days after the start of the reaction, the rate of reaction of methacrolein 83.5% with the same heat transfer medium temperature of 312° C. so that the catalyst layer is keeping a sufficient reaction activity.

COMPARATIVE EXAMPLE 1

The reaction is carried out in the same manner as in Example 1 except that the packing amount of the catalyst in the gas inlet side reaction zone is increased and the heat transfer medium temperature is set to 308° C. In the gas inlet side reaction zone, a mixture of 0.80 kg (670 mL) of the catalyst and 90 mL of aluminum spheres having an external diameter of 5 mm is packed. The length of the catalyst layer of the gas inlet side reaction zone is 1498 mm.

Then, 0.91 kg (760 mL) of the catalyst is packed in the gas outlet side reaction zone. At this time, the length of the catalyst layer of the gas outlet side reaction zone is 1502 mm.

When the temperature of the catalyst layer is measured two days after the start of the reaction, a hot spot having the maximum temperature at the position of 350 mm from the upstream end of the gas inlet side reaction zone is observed and $\Delta T$ at the maximum temperature is 33° C. $Rc(i)$ of the gas inlet side reaction zone is 54.5° C.·m/kg, $CRc(i)$ is 1.0, $Rc(i)$ of the gas outlet side reaction zone is 41.5° C.·m/kg and $CRc(i)$ is 0.76. The rate of reaction of methacrolein is 85.8%, the selectivity to methacrylic acid is 83.8% and the yield of methacrylic acid is 71.9%.

The catalyst layer packed in this condition shows a fast activity lowering and at 30 days after the start of the reaction, the rate of reaction of methacrolein at the initial stage of the reaction can not be maintained even with the increased heat transfer medium temperature of 320° C. From this result, when the catalyst life is defined as the period in which the heat transfer medium temperature reaches 350° C. in the operating procedure of maintaining a certain rate of reaction of methacrolein by raising the heat transfer medium temperature to compensate the activity lowering caused by the catalyst deterioration, it is obvious that the catalyst life should become short in this comparative example though the substantial mass of the catalyst component in the catalyst layer is larger than that in Example 1.

EXAMPLE 2

The reaction is carried out in the same manner as in Example 1 except that the thermocouple protecting tube is not inserted in the reaction tube and the temperature distribution in the catalyst layer during the reaction is not measured. The length of the catalyst layer of the gas inlet side reaction zone is 1495 mm. The length of the catalyst layer of the gas outlet side reaction zone is 1494 mm.

At the time two days after the start of the reaction, the rate of reaction of methacrolein is 83.7%, the selectivity to methacrylic acid is 84.6% and the yield of methacrylic acid is 70.8%. Even at 30 days after the start of the reaction, the rate of reaction of methacrolein is 83.6% with the same heat transfer medium temperate of 312° C. so that the catalyst layer is keeping a sufficient reaction activity.

EXAMPLE 3

The reaction is carried out in the same manner as in Example 1 except that the catalyst layer is divided into three reaction zones and the heat transfer medium temperature and the catalyst packing condition of each reaction zone are changed. In the gas inlet side reaction zone, a mixture of 0.40 kg (330 mL) of the catalyst and 180 mL of aluminum spheres having an external diameter of 5 mm is packed. The length of the catalyst layer of the gas inlet side reaction zone is 1001 mm. Then, in the intermediate reaction zone, a mixture of 0.50 kg (420 mL) of the catalyst and 90 mL of aluminum spheres having an external diameter of 5 mm is packed. The length of the catalyst layer of this reaction zone is 1000 mm. Then, 0.60 kg (510 mL) of the catalyst is packed in the gas outlet side reaction zone. The length of the catalyst layer of the gas outlet side reaction zone is 1004 mm. The reaction is started with the heat transfer medium temperature of 313° C.

When the temperature of the catalyst layer is measured two days after the start of the reaction, a hot spot having the maximum temperature at the position 200 mm from the upstream end of the gas outlet side reaction zone is observed and $\Delta T$ at the maximum temperature is 30° C. $Rc(i)$ of the gas inlet side reaction zone is 52.2° C.·m/kg, $CRc(i)$ is 1.0, $Rc(i)$ of the intermediate reaction zone is 52.4° C.·m/kg, $CRc(i)$ is 1.0, $Rc(i)$ of the raw gas outlet side reaction zone is 47.8° C.·m/kg and $CRc(i)$ is 0.91. The rate of reaction of methacrolein is 83.4%, the selectivity to methacrylic acid is 85.1% and the yield of methacrylic acid is 70.90%. Even at 30 days after the start of the reaction, the rate of reaction of methacrolein is 83.5% with the same heat transfer medium temperature of 313° C. so that the catalyst layer is keeping a sufficient reaction activity.

So far, the method for producing methacrylic acid with respect to the present invention has been explained, however, the present invention is not limited to the above embodiment and can be suitably modified as long as it does not deviate from the scope of the present invention.

INDUSTRIAL APPLICABILITY

According to the present invention, in the method for producing methacrylic acid through the gas-phase catalytic oxidation of methacrolein with molecular oxygen in the presence of a solid oxidation catalyst by the use of a fixed-bed tubular reactor, the local deterioration of the catalyst can be suppressed and the catalyst can be used stably for a long time by not only suppressing the temperature of the hot spot but also making the load of the oxidation reaction in the catalyst layer uniform.

What is claimed is:

1. A method for producing methacrylic acid through gas-phase catalytic oxidation of methacrolein or a methacrolein-containing gas with molecular oxygen or a gas containing molecular oxygen by the use of a fixed-bed multitubular reactor comprising a plurality of reaction tubes each having a catalyst layer therein, wherein the above catalyst layer is divided in the direction of the tube axis of a reaction tube into two or more layers, to thereby provide a plurality of reaction zones, and the catalyst is caused to be present in the catalyst layer in such a way that a reaction load ratio CRc(i) per unit mass of the catalyst in each reaction zone defined by the following equations (1) to (3) becomes 0.8 to 1.0, $$CRc(i) = Rc(i)/RcMAX \quad (1)$$

$$Rc(i) = \left[\sum_{j=1}^{m-1} \frac{\{\Delta T_i(j) + \Delta T_i(j+1)\} \cdot L_i(j)}{2}\right] / Wc(i) \quad (2)$$

$$\Delta T_i(j) = T_i(j) - TB \quad (3)$$

wherein Rc(i) is the reaction load of an i th layer (° C.·m/kg), Li(j) is a distance (m) from a j th measuring point in a i th catalyst layer to the j+1 th measuring point in the direction of the tube axis, Wc(i) is a packing amount (kg) of the catalyst in the i th layer, Ti(j) is a catalyst-layer temperature (° C.) of the j th measuring point in the i th catalyst layer, TB is a heat transfer medium temperature (° C.), RcMAX is a maximum value of Rc(i), n is the number of the reaction zones, and m is the number of the temperature measuring points in the i th catalyst layer; i is 1 to n; i and j are counted in turn from the inlet side of the reaction gas.

2. A method for producing methacrylic acid, wherein a packing condition controlling a substantial mass of the catalyst component per the volume of each reaction zone is determined by the method of claim 1 by using the fixed-bed multitubular reactor provided with the reaction tube in which the temperature distribution in the catalyst layer can be measured, and by using the condition thus determined, the catalyst is packed into the fixed-bed multitubular reactor having the reaction tube in which the temperature distribution in the catalyst layer is not or cannot be measured and the reaction is performed.

3. The method for producing methacrylic acid according to claim 1, wherein the reaction temperature of the gas-phase catalytic oxidation is 250 to 350° C.

4. The method for producing methacrylic acid according to claim 1, wherein the methacrolein-containing gas contains 3 to 9% by volume of methacrolein, 5 to 15% by volume of oxygen, and 5 to 50% by volume of water vapor, and the space velocity of the methacrolein-containing gas is 300 to 3000 hr$^{-1}$.

5. The method for producing methacrylic acid according to claim 1, wherein the maximum value among the distribution of the values obtained by subtracting the temperature of the heat transfer medium from the temperature in the catalyst layer ($\Delta T$) in the direction of the tube axis of the reaction tube is 35° C. or less.

6. The method for producing methacrylic acid according to claim 1, wherein a multitubular reactor provided with a plurality of reaction tubes having an internal diameter of 10 to 40 mm and a heat transfer medium bath are used as the fixed-bed multitubular reactor.

* * * * *